Aug 6, 1974 C. V. BERG Plant Pat. 3,586
WINTER BLUE JUNIPER
Filed March 22, 1973
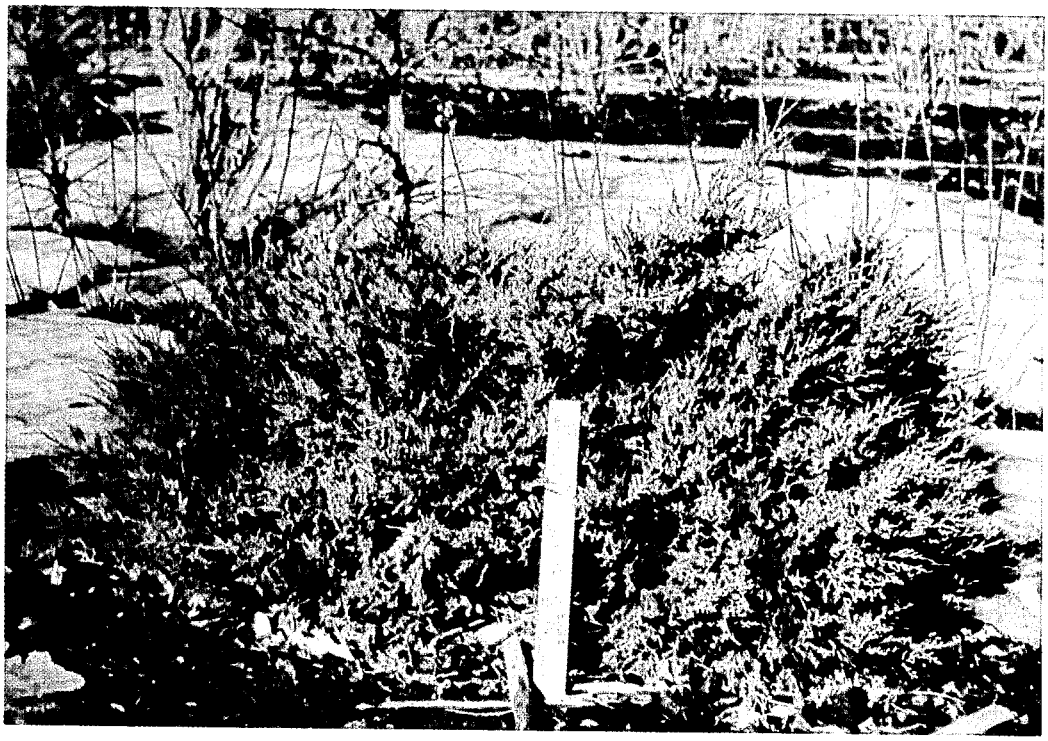

United States Patent Office

Plant Pat. 3,586
Patented Aug. 6, 1974

3,586

JUNIPER SHRUB

Clayton V. Berg, Box 845, Helena, Mont. 59601

Filed Mar. 22, 1973, Ser. No. 343,893
Int. Cl. A01h 7/00
U.S. Cl. Plt.—50 1 Claim

ABSTRACT OF THE DISCLOSURE

A new variety of juniper shrub believed to be a hybrid cross of *Juniperus scopulorum* and possibly *Juniperus horizontalis,* but in any event characterized by definite intense blue color in winter, and winter hardiness.

The new variety was discovered in a group of typically upright *Juniperus scopulorum* seedlings, at the Valley Nursery in Helena, Mont., when it was observed that even as a tiny seedling it had a notable blue winter color, of value from the ornamental viewpoint. Thereafter in the parent, as planted in a container, a hardiness was observed which enabled it to winter well its first 2 or 3 years after discovery. The parent is believed to be a *Juniperus scopulorum* seedling, but could be a hybrid of this and horizontalis or some other juniper of compatible chromosome number.

The new variety has been asexually reproduced by rooting cuttings under mist and also by grafting on Hetzi juniper understock and all the propagules have been found to maintain morphological characteristics as well as the winter color and winter hardiness first observed in the parent.

It is atypical with respect to the classic *Juniperus scopulorum's* pyramidal form, but not necessarily different from known hybrids of *Juniperus scopulorum* and *horizontalis* except for a characteristic heretofore unreported for junipers, of maintaining a blue color in winter, which seems at least as intense as its blue of summer, throughout its foliage in both old and new growth; the winter color being an intense steel blue, changing to a less intense bluish green in late spring with lush new growth.

This new juniper variety has the horizontal branching habit of the blue or glaucous form of Juniperus × media "Pfitzeriana" but is slower growing or more dwarf and has a finer texture than the latter.

During the growing season the new variety has a color as blue as or more blue than the Juniperus × media "Pfitzeriana Glauca"; and has a brighter, more attractive winter color than any of the blue junipers to be seen growing in colder areas of the United States and Canada.

During the winter of dormant season, when all other junipers take a less colorful appearance, it maintains an intense beautiful blue.

The new variety is completely hardy at Helena, Mont., a location which may be deemed representative of the more trying places in non-Alaskan colder regions of the continental United States, where in contrast the blue pfitzer and the other pfitzers often show injury.

This variety is assumed to be a seedling hybrid of *J. scopulorum* and *J. horizontalis*; but since chromosome numbers are the same in most North American and Asian junipers, a cross with one of the other junipers is possibly here represented.

The new variety may be more particularly described as follows.

*General Form Characteristics*

Height: Estimate 5 to 6 feet wide and 2 to 3 feet high in mature form, as estimated from condition at nine years.

Growth rate: Slow to moderate as compared to Juniperus × media "Pfitzeriana."

Form: Very similar in form to Juniperus × media "Pfitzeriana."

Trunk: Normally obscured with foliage.

Branching: Horizontal branching habit; finer texture foliage than, but otherwise essentially the same as Juniperus × media "Pfitzeriana."

Bark: Normal thickness with longitudinal normal spalling and fissuring; color variable with age from yellow brown in younger wood to dull brown to reddish brown in older heavier wood.

Branches: From primary ascending trunk or branches, secondary branches are directed predominately horizontally as in the pfitzer juniper. Branching of primary shoots occurs at slightly less than 45° in most instances.

Branchlets: Branchlets usually arise in an alternate fashion from a primary growing tip at less than 45° angle.

*Leaves*

Disposition and spacing: Mostly opposite with two alignments of pairs alternating at 180° axis displacement.

Size: Length about 5 mm.; width about 1 mm.

Shape: Mainly acicular, awl or needle-like leaves—predominately the typical juvenile form of juniper needles with only the tips of primary branches showing the more adult form of needle growth, similar to what is seen on Juniperus × media "Pfitzeriana" but the juvenile form being present in a much greater proportion on the new variety.

Leaf Color: Leaves exhibit various hues of blue of glaucous color depending on the angle from which a branchlet is viewed. Bluest color is seen looking distal to proximal. Color separately specified below.

*Flower and Fruit*

No flowers or fruit observed to date in propagules, not even in six year old grafts. In parent at about 9 to 10 years age, scanty and immature fruit first observed in winter 1972–1973.

Fruit as seen in first year of development in parent:

*Shape.*—Sub-globose; having fewer and less prominent ridges and irregularities than fruit of *J. scopulorum* " Pyramidalis" seedlings growing in immediate nursery environment. All fruit directed downward on a short curved stalk, as observed typically in nearby *J. scopulorum* "Pyramidalis."

Size: about 4 to 6 mm. diameter, being smaller than fruit of neighboring *J. scopulorum* "Pyramidalis" seedlings.

Color: yellowish green below a silvery "bloom" or coating in February.

The drawing shows the new variety in the dormant state having the typical winter color.

The winter foliage color (for both new growth and old growth in terms of the Munsell-Nickerson Color Fan designations ranges from a very pale blue of 2.5 PB 8/5 to 5 PB 8/5–7/7 to a light blue of 2.5 PB 7/7 to 7.5 PB 8/4 or with some appearance approaching 7.5 B 7/6; in contrast with the color in the growing season, ranging from very light bluish green 7.5 BG 8/5 to 7.5 BG 7/7 and greener.

In fresh foliage specimens taken from the shrub in winter color, it is observed that, in leaflet areas which have been subject to mild rubbing thereby removing a natural coating, the color typically appears as a yellow-green or greenish-yellow, for example, even in the Munsell range of 5 GY 5/6 to GY 5/7.

I claim:

1. A new and distinct variety of spreading juniper shrub substantially as shown and described; characterized by its intense blue winter color, and its winter hardiness in the colder regions of the non-Alaskan continental region of the United States.

No references cited.

ROBERT E. BAGWILL, Primary Examiner